United States Patent [19]
Lyles

[11] Patent Number: 6,001,122
[45] Date of Patent: Dec. 14, 1999

[54] BOOTIE WITH REMOVABLE THERMAL PACK

[76] Inventor: Angela Lyles, 2016 Main SW 1802, Houston, Tex. 77002

[21] Appl. No.: 08/974,050

[22] Filed: Nov. 19, 1997

[51] Int. Cl.[6] .................................................. A61F 7/00
[52] U.S. Cl. ........................... 607/111; 607/108; 607/112; 607/114; 602/5; 602/14; 602/23
[58] Field of Search ..................... 607/96, 104, 108–112, 607/114; 165/46; 602/2, 5, 14, 27, 23

[56] References Cited

U.S. PATENT DOCUMENTS

| | | | |
|---|---|---|---|
| 4,964,402 | 10/1990 | Grim et al. | 607/111 |
| 5,415,624 | 5/1995 | Williams | 607/111 |
| 5,496,358 | 3/1996 | Rosenwald | 607/111 |
| 5,591,221 | 1/1997 | Owens | 607/111 |

*Primary Examiner*—Ryan Carter

[57] ABSTRACT

A bootie is provided including a sleeve having a tubular configuration and adapted to be slid onto a foot of a user. At least one pocket is mounted on the sleeve. At least one thermal pack is included to be removably situated within the pocket.

7 Claims, 2 Drawing Sheets

BOOTIE WITH REMOVABLE THERMAL PACK

BACKGROUND OF THE INVENTION

1. Field of the Invention

The present invention relates to thermal pack holders and more particularly pertains to a new bootie with removable thermal pack for elevating or lowering the temperature of an injured foot and further bandaging the same.

2. Description of the Prior Art

The use of thermal pack holders is known in the prior art. More specifically, thermal pack holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art thermal pack holders include U. S. Pat. No. 4,856,505; U.S. Pat. No. 5,000,176; U.S. Pat. No. 5,113,877; U.S. Pat. No. Des. 341,424; U.S. Pat. No. 4,632,103; and U.S. Pat. No. 5,143,064.

In these respects, the bootie with removable thermal pack according to the present invention substantially departs from the conventional concepts and designs of the prior art, and in so doing provides an apparatus primarily developed for the purpose of elevating or lowering the temperature of an injured foot.

SUMMARY OF THE INVENTION

In view of the foregoing disadvantages inherent in the known types of thermal pack holders now present in the prior art, the present invention provides a new bootie with removable thermal pack construction wherein the same can be utilized for elevating or lowering the temperature of an injured foot.

The general purpose of the present invention, which will be described subsequently in greater detail, is to provide a new bootie with removable thermal pack apparatus and method which has many of the advantages of the thermal pack holders mentioned heretofore and many novel features that result in a new bootie with removable thermal pack which is not anticipated, rendered obvious, suggested, or even implied by any of the prior art thermal pack holders, either alone or in any combination thereof.

To attain this, the present invention generally comprises a sleeve having a top face, a bottom face and a pair of side faces defining a pair of open ends. One of the side faces has a slit formed therein between one of the open ends and a midpoint of the sleeve thus defining a pair of free edges, as shown in FIG. 1. Each free edge has a pile fastener situated along a length thereof. By this structure, the sleeve is adapted to be slid onto a foot of a user with toes of the user extending therefrom When worn, the pile fasteners of the sleeve may be coupled to secure the sleeve to the foot. Next provided is a pair of pockets mounted on the sleeve. The pockets include a top pocket and a bottom pocket each with a rectangular configuration. A closed front edge is situated adjacent to the open end of the sleeve through which the toes of the user pass. A pair of closed side edges are situated along the side faces of the sleeve. An open face is situated at a midpoint of the sleeve and defines a peripheral edge. For permitting the selective scaling of the pocket, an inner surface of the peripheral edge of each pocket has a pair of pile fasteners. FIG. 4 shows one of a pair of flexible thermal packs each with a rectangular configuration. During use, each thermal pack is adapted to be removably situated within the associated pocket. Finally, a securement strap is provided including a metallic eyelet mounted on a first one of the side faces of the sleeve. A strap has a first end connected to the sleeve on a second one of the side faces. The strap includes a top face equipped with a first pile fastener positioned adjacent the first end and a second pile fastener positioned adjacent the second end thereof. As such, the second end of the strap may be threaded through the eyelet and the pile fasteners thereof coupled. This maintains the sleeve secured on the foot of the user and the ice pack of the top pocket in place.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new bootie with removable thermal pack apparatus and method which has many of the advantages of the thermal pack holders mentioned heretofore and many novel features that result in a new bootie with removable thermal pack which is not anticipated, rendered obvious, suggested, or even implied by any of the prior art thermal pack holders, either alone or in any combination thereof.

It is another object of the present invention to provide a new bootie with removable thermal pack which may be easily and efficiently manufactured and marketed.

It is a further object of the present invention to provide a new bootie with removable thermal pack which is of a durable and reliable construction.

An even further object of the present invention is to provide a new bootie with removable thermal pack which is susceptible of a low cost of manufacture with regard to both materials and labor, and which accordingly is then susceptible of low prices of sale to the consuming public, thereby making such bootie with removable thermal pack economically available to the buying public.

Still yet another object of the present invention is to provide a new bootie with removable thermal pack which provides in the apparatuses and methods of the prior art some of the advantages thereof, while simultaneously overcoming some of the disadvantages normally associated therewith.

Still another object of the present invention is to provide a new bootie with removable thermal pack for elevating or lowering the temperature of an injured foot.

Even still another object of the present invention is to provide a new bootie with removable thermal pack that includes a sleeve having a tubular configuration and adapted to be slid onto a foot of a user. At least one pocket is mounted on the sleeve. At least one thermal pack is included to be removably situated within the pocket.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
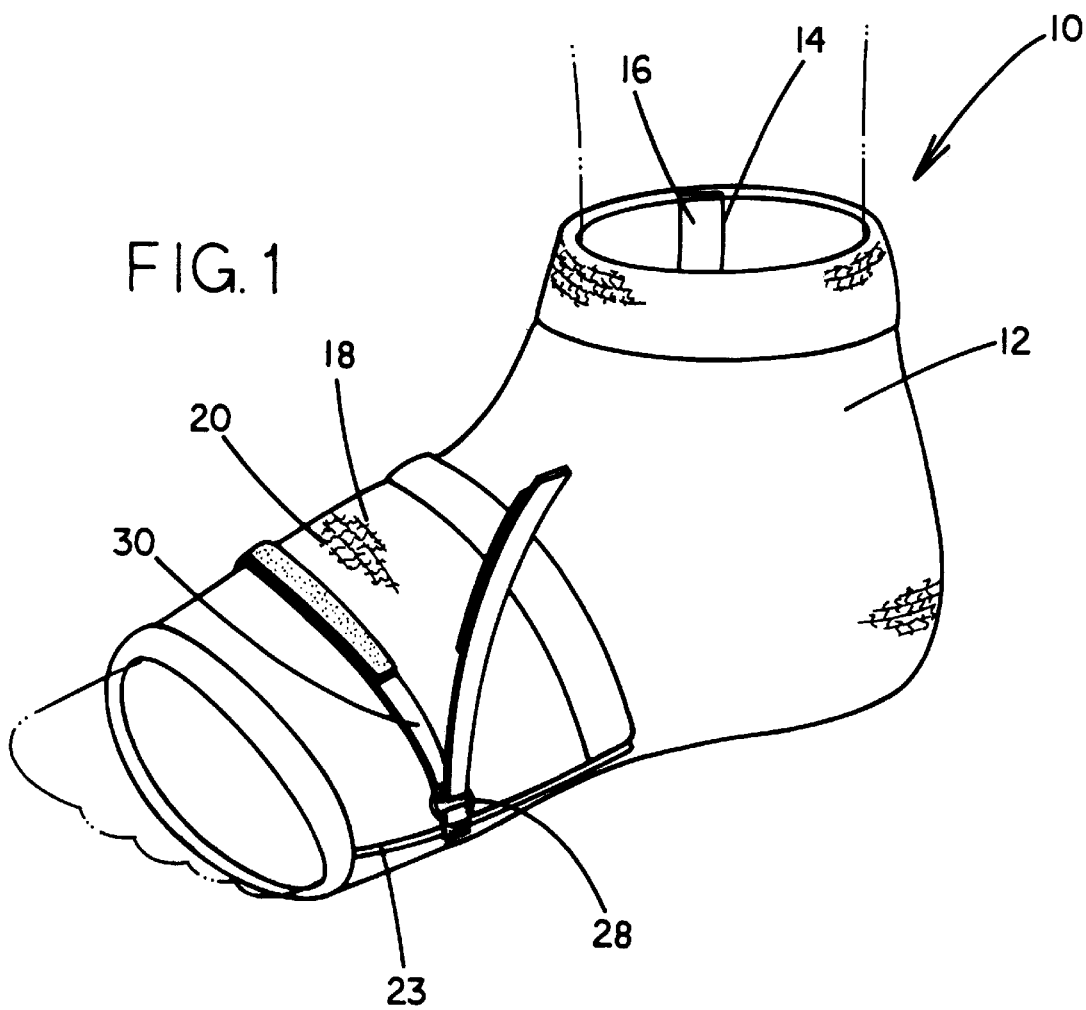
FIG. 1 is a top view of a new bootie with removable thermal pack according to the present invention.

With reference now to the drawings, and in particular to FIGS. 1 through 4 thereof, a new bootie with removable thermal pack embodying the principles and concepts of the present invention and generally designated by the reference numeral 10 will be described.

The present invention, as designated as numeral 10, includes a sleeve 12 having a top face, a bottom face and a pair of side faces defining a pair of open ends. In the preferred embodiment, the sleeve is constructed from a fleece material. As shown in the Figures, each open end is equipped with a cuff. One of the side faces has a slit 14 formed therein between one of the open ends and a midpoint of the sleeve thus defining a pair of free edges, as shown in FIG. 1. Each free edge has a pile fastener 16 situated along a length thereof. By this structure, the sleeve is adapted to be slid onto a foot of a user with toes of the user extending therefrom. Ideally, the sleeve covers an entire ankle of the user. When worn, the pile fasteners of the sleeve may be coupled to secure the sleeve to the foot.

Figure 3:
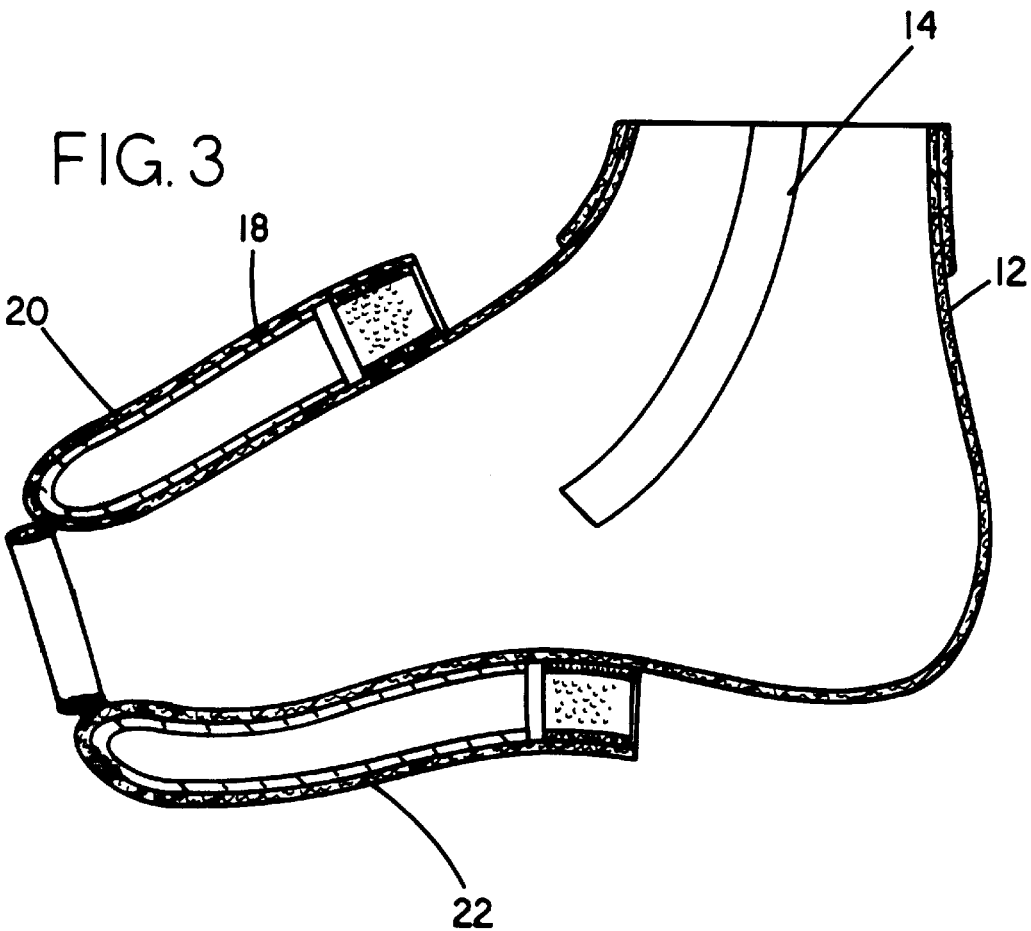
FIG. 3 is a cross-sectional view of the present invention.

Next provided is a pair of pockets 18 mounted on the sleeve. The pockets include a top pocket 20 and a bottom pocket 22 each with a rectangular configuration. A closed front edge of each pocket is situated adjacent to the open end of the sleeve through which the toes of the user pass. A pair of closed side edges are situated along the side faces of the sleeve. Each closed edge preferably takes the form of a pleat 23. An open face of each pocket is situated at a midpoint of the sleeve and defines a peripheral edge. The open face of the top pocket is preferably situated adjacent the instep on the inside of the ankle. As shown in FIG. 3, each pocket is defined by an integral extension of the sleeve adjacent the bottom one of the open ends thereof. For permitting the selective sealing of the pocket, an inner surface of the peripheral edge of each pocket has a pair of pile fasteners. As an option, each pocket may be lined with an insulating or water impermeable material.

Figure 4:
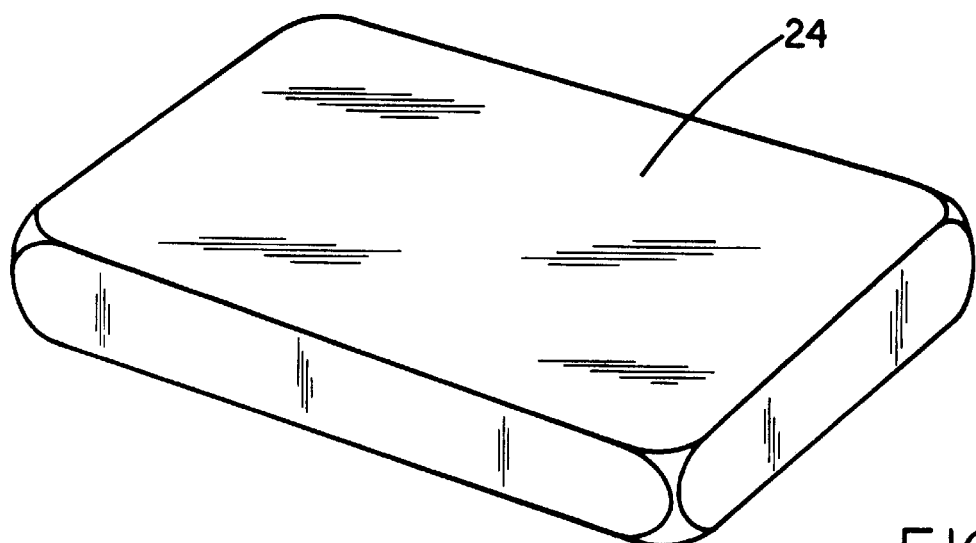
FIG. 4 is a perspective of one of the thermal packs of the present invention.

FIG. 4 shows one of a pair of flexible thermal packs 24 with a rectangular configuration. During use, each thermal pack is adapted to be removably situated within the associated pocket. It should be noted that the thermal packs may either consist of cold or hot packs.

Figure 2:
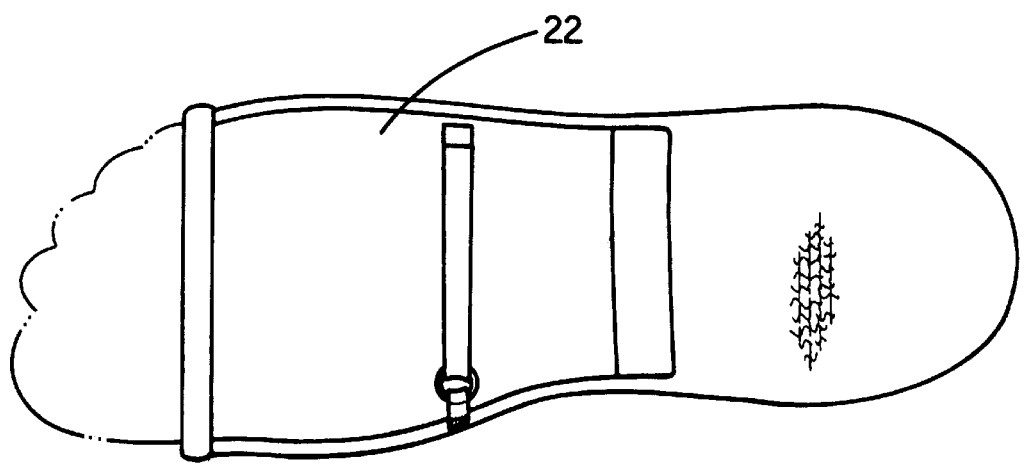
FIG. 2 is a top view of the present invention.

Finally, a securement strap is provided including a metallic eyelet 28 mounted on a first one of the side faces of the sleeve adjacent a midpoint of the top pocket. A strap 30 has a first end connected to the sleeve on a second one of the side faces. The strap includes a top face equipped with a first pile fastener positioned adjacent the first end and a second pile fastener positioned adjacent the second end thereof. As such, the second end of the strap may be threaded through the eyelet and the pile fasteners thereof coupled. This maintains the sleeve secured on the foot of the user and the ice pack of the top pocket in place. As shown in FIG. 2, an additional strap is associated with the bottom pocket with structure identical to that of the strap of the top pocket.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An bootie comprising, in combination:

a sleeve having a top face, a bottom face and a pair of side faces defining a pair of open ends, one of the side faces having a slit formed therein between one of the open ends and a midpoint of the sleeve thus defining a pair of free edges, each free edge having a pile fastener situated along a length thereof, whereby the sleeve is adapted to be slid onto a foot of a user with toes of the user extending therefrom and the pile fasteners attached to secure the sleeve to the foot;

a pair of pockets mounted on the sleeve including a top pocket and a bottom pocket, the top pocket being mounted to the top face of the sleeve, the bottom pocket being coupled to the bottom face of the sleeve, each of the pockets having a rectangular configuration and a closed front edge situated adjacent to the open end of the sleeve through which the toes of the user pass, a pair of closed side edges situated along the side faces of the sleeve and an open face situated at a midpoint of the sleeve and defining a peripheral edge of the pocket, an inner surface of the peripheral edge of each pocket having a pair of pile fasteners for permitting selective sealing of the pocket;

a pair of flexible thermal packs each with a rectangular configuration and adapted to be removably situated within the pockets; and a securement strap including a metallic eyelet mounted on a first one of the side faces of the sleeve and a strap having a first end connected to the sleeve on a second one of the side faces, the strap having a top face with a first pile fastener positioned adjacent the first end and a second pile fastener positioned adjacent the second end thereof, whereby the second end of the strap may be threaded through the eyelet and the pile fasteners thereof coupled to maintain the sleeve secured on the foot of the user and the thermal pack of the top pocket in place.

2. A bootie comprising:

a sleeve having a tubular configuration and adapted to be slid onto a foot of a user;

a pair of pockets mounted on the sleeve including a top pocket and a bottom pocket, the top pocket being mounted to a top face of the sleeve, the bottom pocket being mounted to a bottom face of the sleeve, each of the pockets having a rectangular configuration and a closed front edge situated adjacent to the toes of the user, a pair of closed side edges situated along the sleeve and an open face situated at a midpoint of the sleeve and defining a peripheral edge of the pocket, an inner surface of the peripheral edge of each pocket having a pair of pile fasteners for permitting selective sealing of the pocket; and at least one thermal pack adapted to be removably situated within one of the pockets.

3. The bootie as set forth in claim 2 wherein a securement strap is mounted on the sleeve over the pocket.

4. The bootie as set forth in claim 3 wherein the securement strap includes an eyelet and a strap.

5. The bootie as set forth in claim 2 wherein the sleeve has a slit formed therein defining a pair of free edges to which a pair of pile fasteners are mounted.

6. The bootie as set forth in claim 2 wherein the sleeve has a pair of open ends such that when worn, toes of the user extend therefrom.

7. The bootie as set forth in claim 2 wherein the thermal pack is flexible.

* * * * *